United States Patent
Reitter

(10) Patent No.: US 6,263,231 B1
(45) Date of Patent: Jul. 17, 2001

(54) DIAGNOSTIC IMAGING APPARATUS HAVING AN IMAGE SIGNAL PROCESSOR WITH SPATIAL-FREQUENCY FILTERING WITH A SETTABLE BANDPASS CHARACTERISTIC

(75) Inventor: Josef Reitter, Moehrendorf (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/429,403

(22) Filed: Oct. 28, 1999

(30) Foreign Application Priority Data

Oct. 28, 1998 (DE) ................................................ 198 49 764

(51) Int. Cl.$^7$ ........................................................ A61B 5/05
(52) U.S. Cl. ........................ 600/425; 378/98; 378/21; 378/62; 345/428; 345/429; 382/103; 382/132; 382/131; 324/307; 128/922
(58) Field of Search ............................... 600/425, 427, 600/437, 410; 378/4, 6, 21, 98, 98.5, 901, 62; 345/428, 429; 382/103, 131, 128, 132; 324/307; 128/920, 922

(56) References Cited

U.S. PATENT DOCUMENTS

| | | |
|---|---|---|
| 4,271,389 * | 6/1981 | Jacobi et al. ........................ 324/58.5 |
| 4,907,156 | 3/1990 | Doi et al. . |
| 5,257,022 | 10/1993 | Irie . |
| 5,343,390 * | 8/1994 | Doi et al. ........................ 364/413.16 |
| 5,360,006 * | 11/1994 | Geiser et al. ........................ 128/653.1 |
| 5,384,602 * | 1/1995 | Bossaert et al. ...................... 348/628 |
| 5,431,161 * | 7/1995 | Ryals et al. ........................ 128/653.1 |
| 5,864,630 * | 1/1999 | Cosatto et al. ........................ 382/103 |
| 6,018,600 * | 1/2000 | Levin et al. ........................... 382/284 |
| 6,111,975 * | 8/2000 | Sacks et al. ........................... 382/103 |
| 6,118,887 * | 9/2000 | Cosatto et al. ........................ 382/103 |

FOREIGN PATENT DOCUMENTS

| | | |
|---|---|---|
| 195 00 338 | 2/1996 | (DE) . |
| WO 86/01920 | 3/1986 | (WO) . |

* cited by examiner

Primary Examiner—Marvin M. Lateef
Assistant Examiner—Eleni Mantis Mercader
(74) Attorney, Agent, or Firm—Schiff Hardin & Waite

(57) ABSTRACT

An diagnostic imaging apparatus for acquiring image information representing at least one region of an examination subject, generates image signals that correspond to the acquired image information and has a signal processor to which the image signals are fed. The signal processor subjects the image signals to spatial-frequency filtering with a controlled bandpass characteristic, in order to be able to display subjects situated in the passband of the bandpass characteristic more clearly with respect to their dimensions.

8 Claims, 3 Drawing Sheets

DIAGNOSTIC IMAGING APPARATUS HAVING AN IMAGE SIGNAL PROCESSOR WITH SPATIAL-FREQUENCY FILTERING WITH A SETTABLE BANDPASS CHARACTERISTIC

BACKGROUND OF THE INVENTION

1. Field of the Invention

The present invention relates to a diagnostic imaging apparatus for acquiring image information representing at least one region of an examination subject, which generates image signals that correspond to the acquired image information, of the type having a signal processor, to which the image signals are fed, which subjects the image signals to spatial-frequency filtering with a bandpass characteristic, and which feeds the thus-acquired signals to a display for image representation.

2. Description of the Prior Art

Diagnostic imaging systems of this type are known, for instance which have an X-ray source and an X-ray receiver cooperating therewith that emits image signals corresponding to the received X-rays.

In many applications of such diagnostic imaging systems, for instance in the localization of kidney stones in lithotripsy, it is a problem to reliably distinguish the kidney stones from the background noise. Specifically in adipose patients, the kidney stones are displayed in very poor contrast in the fluoroscopy mode, so that the useful signal, that is, the signal components representing the kidney stone, are significantly below the noise level. This problem is intensified by the fact that the treatment in recidivist cases ensues at an ever earlier time, that is, at a time at which the size of the stones is still very small.

If an unambiguous localization of the kidney stone is not possible, treatment can be very difficult or in certain circumstances impossible.

It may be attempted to improve the signal/noise interval by conventional methods, for instance by integrating several images and subsequently windowing the resultant image. In any case, due to the motion of the stone caused by the patient's breathing, it is not possible to select high integration times, since otherwise the kidney stone would be displayed blurred, or would not be displayed at all because of poor contrast. In addition, windowing is only suitable in cases where homogenous structures are imaged, which is usually not the case in the localization of kidney stones.

The known measure of edge highlighting, which uses spatial-frequency filtering with a high-pass characteristic, usually only makes the signal/noise ratio worse.

Of course, in the case of radiographic diagnostic systems, the image quality can be improved by increasing the X-ray dose; however, this is possible only to a limited degree in view of the radiation load on the patient.

The text "Lexikon der Computergrafik und Bildverarbeitung" (Vieweg Verlagsgesellschaft, 1994, pages 141,142, 340 and 341) teaches performing a spatial filtering with a bandpass characteristic, with the result that noise components beyond the upper limit frequency of the bandpass characteristic are suppressed, and subjects of a size exceeding the lower limit frequency of the bandpass characteristic and not visibly displayed or are displayed only in an attenuated manner. Thus, an improvement of the signal/noise ratio is achieved, while an enhancement of the contrast in the display of preferred subjects is achieved as well.

The application of bandpass filters in image processing is also described in German Patent Specification 38 26 285, PCT Application WO 86/01 920, German Patent Specification 195 00 338 and German Patent Specification 41 09 159.

SUMMARY OF THE INVENTION

An object of the present invention is to provide a diagnostic imaging apparatus of the type described above with which it is possible to display the respective subjects clearly even under unfavorable conditions, for instance in cases where the image signals have a very low signal/noise ratio.

This object is inventively achieved in a diagnostic imaging apparatus for acquiring image information representing at least one region of an examination subject, which generates image signals from the acquired image information, having a signal processor, to which the image signals are fed, which subjects the image signals to spatial-frequency filtering with an adjustable bandpass characteristic, and which feeds the thus-acquired signals to a display for image representation, wherein the bandpass characteristics are set by at least one of the following types of units: (a) a unit for entering the minimum dimension of a subject that is to be displayed, which adjusts the upper limit frequency of the bandpass characteristic such that it has at least the value required in order to display subjects of the entered minimum dimension; (b) a unit for entering the maximum dimension of a subject that is to be displayed, which adjusts the lower limit frequency of the bandpass characteristic such that it does not fall below the value required in order to display subjects of the entered maximum dimension; (c) a unit for calculating the spectral characteristics of the noise that is superimposed on the image signals, which adjusts the upper limit frequency of the bandpass characteristic dependent on the calculated spectral characteristics of the noise; and (d) a unit for entering the contour of a subject that is to be displayed which has a pattern detector, which examines the image signals for the presence of a subject having the entered contour, and which adjusts the upper and lower limit frequencies of the bandpass characteristic dependent on the smallest dimension and the largest dimension of the detected subject, given the presence of such a subject in the image signals.

Because the unit for calculating the spectral characteristics of the noise that is superimposed on the image signals adjust the upper limit frequency of the bandpass characteristic dependent on the calculated spectral characteristics of the noise, the upper limit frequency of the bandpass characteristic is adjusted such that the spectral section that has the lowest frequency and that exceeds a specific amplitude, and the spectral sections having a higher frequency than this, are suppressed. Because the unit for entering the minimum dimensions of a subject that is to be displayed sets the upper limit frequency of the bandpass characteristic such that this has at least the value required in order to display subjects of the entered minimum dimension, it is guaranteed that useful information is not suppressed at the same time. Because the unit for entering the maximum dimension of a subject that is to be displayed sets the lower limit frequency of the bandpass characteristic such that it does not fall below the value required in order to display subjects of the entered maximum dimension, it is guaranteed that signal components which do not originate from the subject that is to be displayed, but rather relate to larger objects, are suppressed or attenuated, as needed, in the interest of improving contrast. Because the unit for entering the contour of a subject that is to be displayed, which has a pattern recognition stage, examines the image signals for the presence of a subject of the entered contour and adjusts the filter parameters of the bandpass characteristic accordingly, an additional contrast enhancement (signal/noise ratio) of the detected subjects is effectuated, so that, by employing pattern recognition, which is known, it is possible to improve the recognizability of specific subjects and possibly to capture their movement.

By means of the invention, it is possible to suppress, in the image representation, movements of a subject which are caused by a patient's respiratory activity, namely by generating a series of images of the subject, and, of the generated images, only a section that surrounds the subject is displayed on the monitor. If the aforementioned unit for entering the contour of the subject with a pattern recognition stage is used, the image signals are analyzed dependent on the entered contour to identify the position of the subject in the individual images of the series, and the signal processor selects the sections that are to be displayed of the individual images of the series. This results in the subject to be displayed always being displayed at substantially the same location in the displayed sections of the series of images on the monitor. An image stabilization is thereby achieved.

It is also possible using the invention to avoid unsharpness which is caused by a patient's respiration in images of longer generation time, for instance the exposure time in a radiographic diagnostic apparatus. This is accomplished by generating a series of images of a subject and, of the generated images, only a section that surrounds the subject to be displayed is respectively used. The aforementioned unit for entering the contour of the subject to be displayed has a recognition stage, which analyzes the image signals dependent on the entered contour to identify the position of the subject in the individual images of the series. The signal processor selects the sections that are used of the individual images of the series so that the subject is always located at substantially the same location in the sections of the individual images of the series, and the sections of the individual images of the series are integrated to form a total image. The total image then corresponds to a normal image that is generated during a total image generation time corresponding to the sum of the image generation times of the individual images, though it represents the subject more sharply than would be the case in a normal image. In the case of an inventive radiography diagnostic device, this means that the total image corresponds to a normal image that was produced with the sum of the radiation doses of the individual images of the series but is sharper than such a normal image.

In another version of the invention, the diagnostic imaging apparatus has a therapeutic radiation source for generating radiation which is focused to a focal region that is situated in the same region from which the image information originates. A series of images is generated of a region that is to be treated with the radiation, and the aforementioned unit for entering the contour of the region to be treated, with a pattern recognition stage, analyzes the image signals dependent on the entered contour to identify the position of the region to be treated in the individual images of the series. The therapeutic radiation source can be activated for emitting radiation only when the aforementioned imaging of the focal region by diagnostic imaging apparatus substantially coincides with the position of the image of the region that is to be treated. It is thus impossible for the radiation source to be activated if the region to be treated is not located in the focal region of the radiation.

In another embodiment of the version of the inventive diagnostic imaging apparatus having a radiation source, an adjustment unit is provided for displacing the focal region of the focused radiation and the region that is to be treated relative to each other, and a series of images is generated of a region that is to be treated with the radiation. The aforementioned unit for entering the contour of the region to be treated, having a pattern recognition stage, analyzes the image signals dependent on the entered contour for the position of the region to be treated in the individual images of the series, and actuates the adjustment unit that the aforementioned image of the focal resin obtained by the diagnostic imaging apparatus substantially coincides with the position of the image of the region to be treated. If the region to be treated moves, the focal region is thus moved so as to follow these movements, so that it is impossible for body regions other than the region to be treated to be located in the focal region of the radiation.

The pattern recognition stage can correspondingly adjust the upper and lower limit frequencies of the bandpass characteristic dependent on the smallest and the largest dimensions of the detected subject, or of the region to be treated.

DESCRIPTION OF THE PREFERRED EMBODIMENTS

Figure 1:
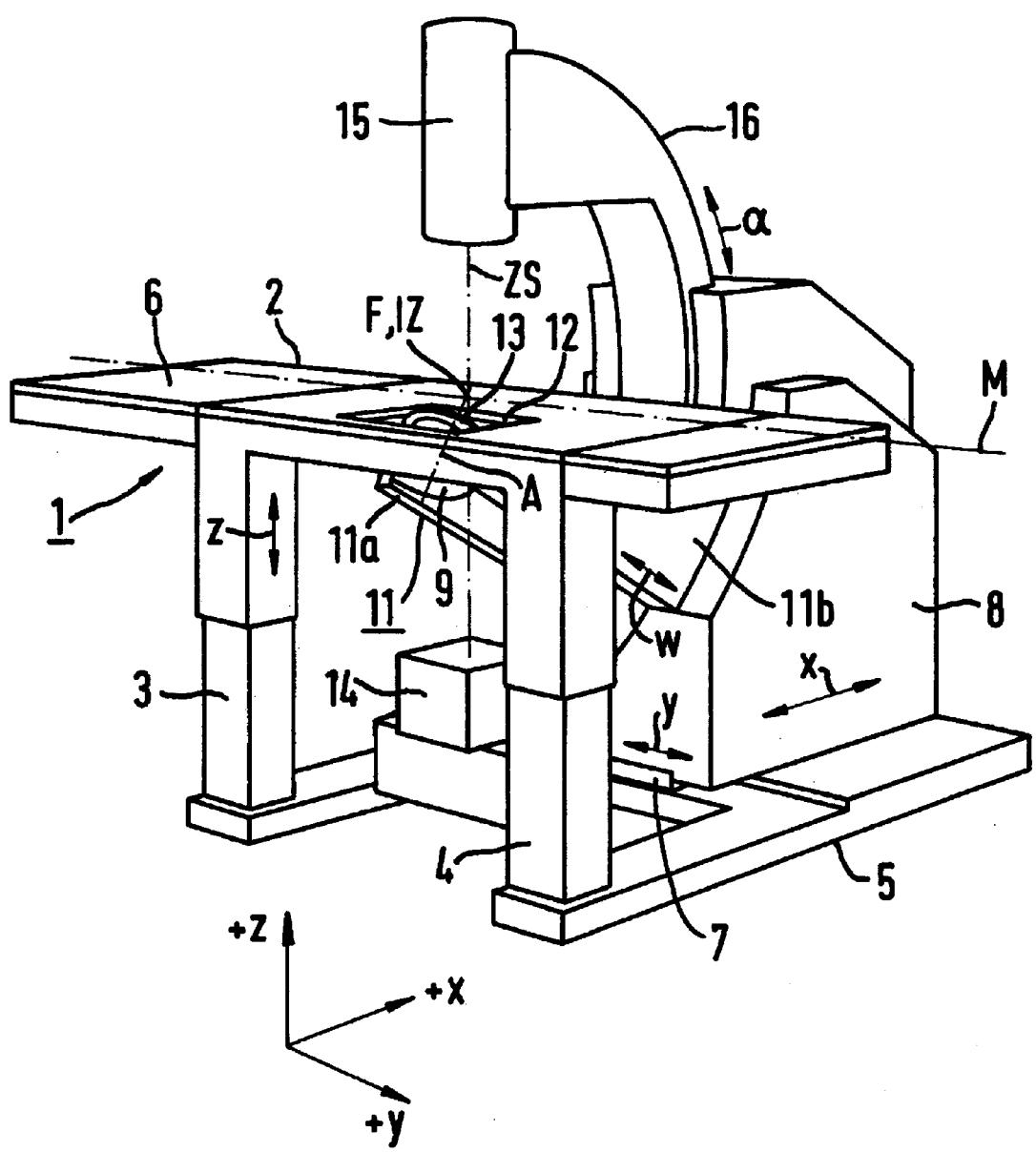
FIG. 1 is a perspective view of an inventive radiographic diagnostic imaging apparatus.

As illustrated in FIG. 1, the inventive radiographic diagnostic imaging apparatus has a support table 1 for a subject to be examined or treated, for instance a patient. The height of the support plate 22 of the support table 1 can be adjusted by two telescoping columns 3,4 relative to a base 5 in the direction of the double arrow z, and thus parallel to the z-axis of a Cartesian coordinate system illustrated in FIG. 1.

A sled 7 is mounted on the base 5 such that it can be displaced linearly in the direction of the longitudinal axis of the support plate 2, which extends parallel to the y-axis of the spatial coordinate system, this being represented by a double arrow referenced y. A support element 8 is mounted on the sled 7 such that it can be displaced longitudinally in a direction transverse to the longitudinal axis of the support plate 2 and thus parallel to the x-axis of the coordinate system. This is indicated by the double arrow x.

The displacement of the support element 8, the sled 7 and the support plate 2 in the directions of the respective double arrows x,y,z is accomplished by suitable motors, particularly electromotors, and if necessary by suitable gearings (transmissions), particularly of a mechanical nature (this is not detailed).

An X-ray radiator 14, as an X-ray source, is mounted at one end of a C-arm and a radiographic image intensifier 15, which is a component of a radiographic image intensifier-te$_1$envision chain, is mounted opposite to the X-ray radiator 14 on the C-arm 16. The C-arm 16 is mounted at the support element 8 such that it can be displaced along its perimeter in the direction of the curved double arrow α. More exactly, the C-arm 16 can be rotated around its center axis M, with the center ray ZS of the X-ray beam emanating from the X-radiator 14 intersecting the center axis M of the C-arm 16 at a right angle in the case of this exemplary embodiment.

Furthermore, the C-arm 16 is attached to the support element 8 such that the center axis of the C-arm 16 and the center ray ZS proceed through an isocenter IZ. The center ray ZS of the X-ray diagnostic apparatus thus proceeds through the isocenter IZ for arbitrary rotational positions of the C-arm 16.

In the exemplary embodiment, the X-ray diagnostic apparatus also a focused acoustic wave source 9, which can be an electromagnetic pressure pulse source of the type described in European Application 0 372 119. The source 9 has an acoustic axis A on which lies the focal zone F of the acoustic pressure pulses that are generated by the source 9. For more detailed information relating to electromagnetic pressure pulse sources, see U.S. Pat. No. 4,647,505 and European Application 0 188 750, whose disclosures are incorporated herein by reference.

The source 9 is attached to a source carrier 11 having two arms 11a and 11b. The carrier 11 is attached in turn to the support element 8 such that it can be displaced longitudinally. The arrangement such that the focus F is located in the isocenter IZ above the support surface 6 of the support plate 2. The acoustic axis A of the source 9 thus also proceeds through the isocenter IZ. The source 9 projects through the opening 12 of the support plate 2 with a bellows-type flexible coupling cushion 13 that serves for acoustically coupling the source 9 to a patient who is to be treated.

As a result of the described device movements, it is possible to set an orientation of the patient, on one hand, and of the X-ray 14 and the radiographic image intensifier 15, relative to one another, in which orientation a subject of the patient is located in the radiation beam of the X-rays. In particular, it is possible to orient the patient and the source 9 relative to each other such that a region of the patient which is to be treated with the pressure pulses, that are generated by the source 9, is located in the focal zone F of the pressure pulses.

Figure 2:
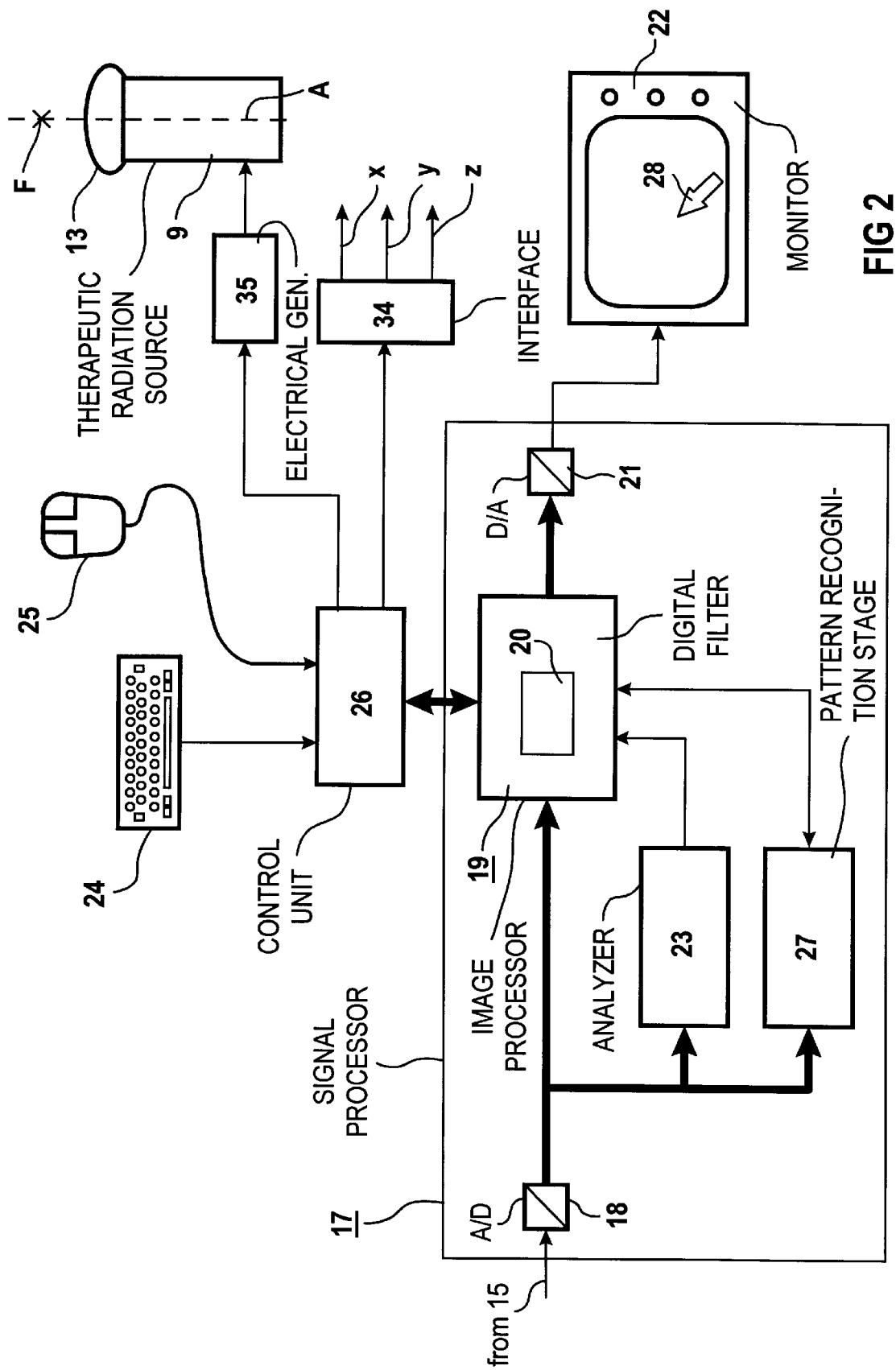
FIG. 2 is a schematic block diagram of a part of the radiographic diagnostic imaging apparatus illustrated in FIG. 1.

As depicted in FIG. 2, the inventive radiographic diagnostic apparatus has a signal processor 17, to which the output signals of the radiographic image intensifier-television chain, that includes the radiographic image intensifier 15, are fed. Subsequent to digitizing by an analog/digital converter 18 (this converter can be omitted if the radiographic image intensifier-television chain already supplies digital image signals), these image signals reach a digital filter 20, which is contained in an image processor 19 and which subjects the image signals to a spatial-frequency filtering with a bandpass characteristic. The thus obtained signals go to a monitor 22 via a digital/analog converter, and the monitor displays the corresponding images.

The upper limit frequency of the bandpass characteristic can be calculated dependent on the spectral characteristics of the noise that is superimposed on the image signals. For this purpose, an analyzer 23 is provided for calculating the spectral characteristics of the noise that is superimposed on the image signals, to which the digital image signals are fed. The analyzer 23 calculates the spectral characteristics of the noise and sets the upper limit frequency of the bandpass characteristic of the digital filter 20. This upper limit frequency is set such that the highest amplitude noise components will be filtered out by virtue of this upper limit.

It is also possible to enter an upper limit frequency of the bandpass characteristic via an input system, such as a keyboard 24 or a mouse 25 and monitor 22, which are connected to a control unit 26 that is connected to the signal processor 17. Specifically, selection (entry) of the upper limit frequency is accomplished by entering the smallest dimension of the subject that is to be shown in the images which are displayed on the monitor 22.

The digital filter 20 sets the upper limit frequency of the bandpass characteristic according to the value supplied by the analyzer 23, if the upper limit frequency which corresponds to the entered smallest dimension of a subject is smaller than that which was supplied by the analyzer 23. Conversely, the digital filter 20 sets the upper limit frequency of the bandpass characteristic according to the entered smallest dimension of the subject if this is above the value supplied by the analyzer 23. This guarantees that signal sections which are not relevant to diagnosis are suppressed, in the interest of noise reduction.

The lower limit frequency of the bandpass characteristic is set by the digital filter 20 according to a value for the largest dimension of the respective subject, which is entered via the keyboard 24, or by the mouse 25, and using the monitor 22.

Thus, in a first mode of operation of the inventive radiographic diagnostic apparatus, the images displayed on the monitor 22 are optimized in terms of their quality, by suppressing noise components inasmuch as this is diagnostically feasible, as well as by eliminating or attenuating (depending on the prevailing requirements) the display of larger subjects which could mask the image information of the diagnostically relevant subject.

The signal processor means 17 also can include a pattern recognition stage 27, to which the digital image signals are likewise fed. Thus, in a second mode of operation of the inventive radiographic diagnostic device, the contour of a subject that is to be displayed is entered via keyboard 24 or the mouse 25 and using the monitor 22, and the pattern recognition stage 27 then analyzes the image signals dependent on the entered contour so as to determine whether these image signals contain components relating to a subject having the entered contour. If they do, the pattern recognition stage 27 sends corresponding data to the digital filter 20, which subsequently sets the upper and lower limit frequencies of the bandpass characteristic, if necessary also dependent on output data of the analyzer 23, so that the upper limit frequency corresponds to the smallest dimension, and the lower limit frequency corresponds to the largest dimension, of the detected subject having the entered contour.

Figure 3:
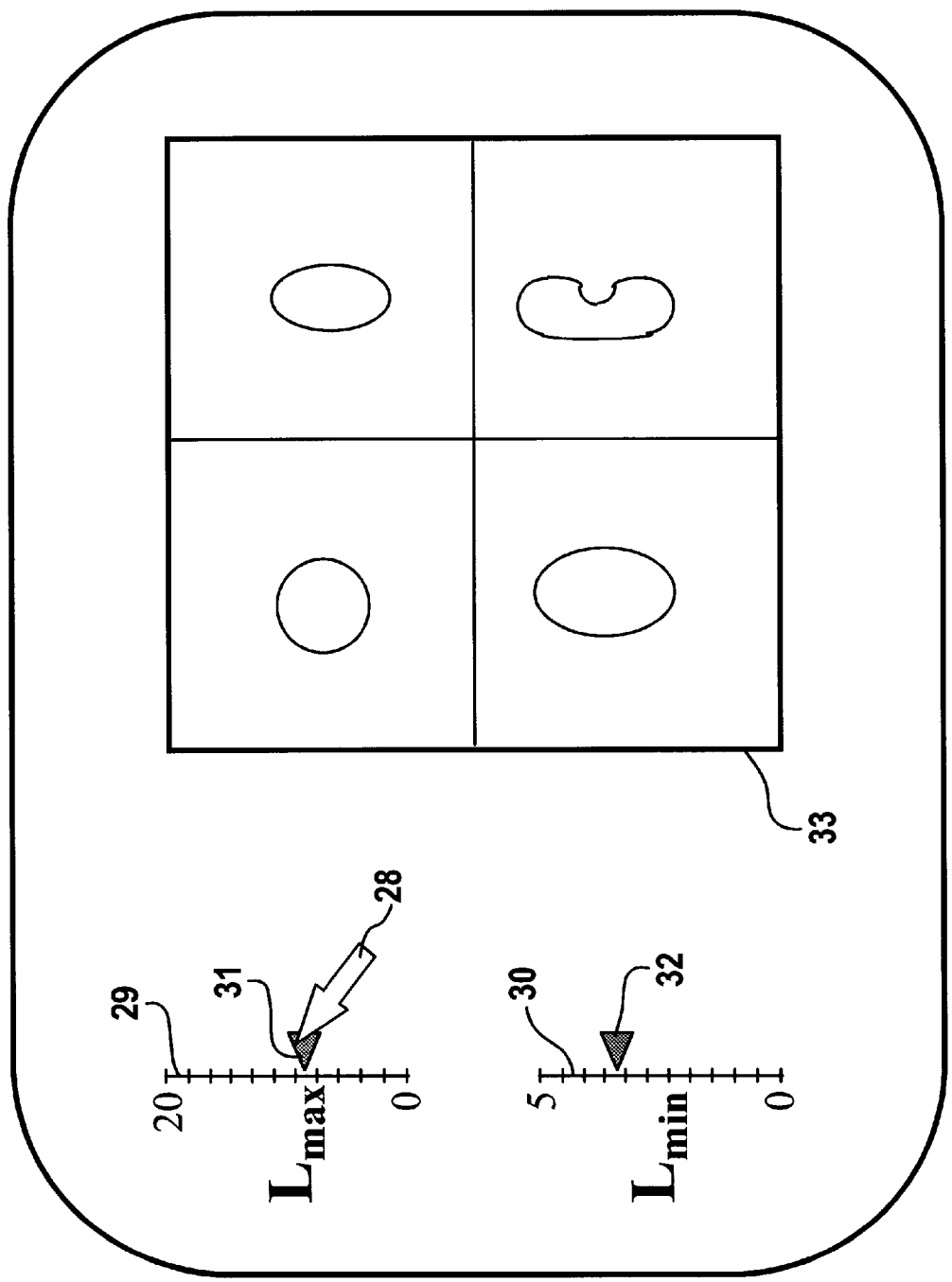
FIG. 3 shows an exemplary portion of the operator interface of the inventive radiographic diagnostic imaging apparatus depicted in the FIGS. 1 and 2.

In the exemplary embodiment, the entry of the smallest or largest dimension of a subject that is to be displayed can be accomplished by means of the keyboard 24, as described above. This entry is preferably accomplished, however, by means of the mouse 25 and the monitor 22, namely by sliding cursors 31 and 32 to selected values using the mouse pointer 28, on respective scales 29 and 30 on the screen of the monitor 22. The scales 29 and 30 respectively illustrate the largest dimension $L_{max}$ and the smallest dimension $L_{min}$, respectively, as is illustrated in FIG. 3.

The entry of the contour of the subject is accomplished by means of the mouse pointer 28 by clicking a predetermined contour in a table 33 which corresponds precisely, or at least approximately, to the contour that is to be detected.

Optionally, for entering the contour of the subject to be displayed, it is possible to prepare an image with a high dose of X-radiation and a correspondingly good signal/noise ratio, and then to trace the corresponding contour in this image using the mouse pointer 28.

Finally, it is also possible to enter the contour by moving the mouse pointer 28 on the surface of the screen of the monitor 22 in a manner corresponding to a desired contour.

A third operational mode of the inventive radiographic diagnosis means serves for preparing particularly noise-free images of a subject which moves while the image is being prepared, for instance due to the respiratory activity of a patient.

In this operational mode, first the contour of the subject is entered by one of the methods described above. Then, a series of images is captured, the exposure time of the individual images being selected according to the respective conditions so that no notable motion unsharpnesses can occur. The number of images of the series is selected such that the total dosage of the X-rays that is employed for capturing the series of images at least approximately corresponds to the dose that would be necessary in order to acquire a similarly noise-free image with a single exposure.

For each of the individual images of the series, the pattern recognition stage 27 analyzes the position assumed by the subject that is to be displayed, and it sends corresponding data to the image processor 19. The image processor 19 selects an equally large section from each of the individual images of the series such that the subject assumes the same position within this section in all images of the series. The image processor 19 integrates the thus-acquired sections and displays the corresponding image on the monitor 22.

With respect to its signal/noise ratio, the thus-acquired image corresponds to a single image captured with an exposure time corresponding to the total exposure time of the series of images, but it does not contain motion unsharpnesses.

In a fourth operational mode of the inventive radiographic diagnostic apparatus, the same procedure is followed as in the above described methods of operation, but there is no integration of the individual images of the series. In this way, cine sequences are possible, in which the diagnostically relevant region appears stationary, although it is really moving.

As already mentioned, it is possible to treat a patient with focused acoustic waves, namely with pressure pulses, using the source 9, for instance for lithotripsy.

In order to guarantee that the region of the patient that is to be treated, i.e. the stone that is to be disintegrated, is really located in the focal zone F during the treatment, two images of the region of the patient that is to be treated are prepared, at respectively different directions of the center ray ZS, for which purpose the C-arm 15 is moved in the α-direction. Using these two images, an alignment of the patient and the source 9 relative to each other can occur by moving the device in the x, y and z directions, so that the region that is to be treated is located in the focal zone F. In the inventive radiographic diagnostic device, this occurs by entering the contour of the region to be treated using one of the procedures previously described. The pattern recognition stage 27 analyzes the image signals that correspond to the images obtained at different radiation directions to identify the position of the region that is to be treated in each of these images. The pattern recognition stage 27 delivers corresponding data to the control unit 26, which controls the motors that are allocated to the x, y and z directions, via a suitable interface 34, so that the region to be treated comes to reside in the focal zone F.

Since, particularly in the case of the treatment of kidney stones, a not insignificant movement of the kidney stones occurs as a result of the respiratory activity of the patient, it is ensured in a first mode of operation, which makes use of the source 9, that the emission of shock waves occurs only when the region that is to be treated is actually located in the focal zone F. This is accomplished, following the first alignment which is accomplished in the above described manner, by continuously generating a series of images of the region that is to be treated during treatment, preferably with a reduced X-ray dose, and the images of this series are subsequently respectively analyzed by the pattern recognition stage 27 to identify where the region that is to be treated is located in each image. Corresponding data are supplied via the image processor 19 to the control unit 26, which enables an electrical generator 35 that drives the source 9 only when the region that is to be treated is located in the focal zone F. The image processor 19 recognizes this from the fact that the projection of the focal zone F on the input screen of the radiographic intensifier 15 lies within the image of the region that is to be treated on the input screen of the X-ray image intensifier 15, which means that the center ray ZS passes through the image of the region to be treated on the input screen of the X-ray image intensifier 15. The individual images of the series can be prepared with a very low dose, since a good signal/noise ratio is achieved as a result of the spatial-frequency filtering.

Alternatively or in addition, in a second mode of operation involving the source 9 the data acquired by the pattern recognition stage 27 relating to the position of the region to be treated are used by the control unit 26 to control the motors for the x, y and z directions such that the region to be treated always stays in focus; that is, the image of the region to be treated on the input screen of the X-ray intensifier lies on the center ray ZS.

Further details of the spatial-frequency filtering used in the inventive radiographic diagnostic apparatus are described in the book "Bildgebende Systeme für die medizinische Diagnostik" (Heinz Morneburg, $3^{rd}$ ed., 1995, Publicis MCD: 341–347).

In the exemplary embodiment, the radiographic diagnostic apparatus has a number of different modes of operation, but a radiographic diagnostic apparatus need not necessarily have all of these modes of operation.

The invention has been described in the context of example of a radiographic diagnostic apparatus having a source of focused acoustic waves, but it can also be used in a radiographic diagnostic apparatus without such a source.

The invention can also be used in radiographic CT devices (computed tomography) as well as in other imaging systems that do not operate on the basis of X-rays, such as ultrasound devices or MR devices.

The mode of operation described in connection with the exemplary embodiments wherein a series of images is obtained can be realized particularly advantageously using an ultrasound imaging system, since such systems, as opposed to radiographic diagnostic systems, do not entail the danger of an undesirable radiation load on the patient.

The invention has been described using the example of a medical application, but the invention also can be used outside the field of medicine.

Although modifications and changes may be suggested by those skilled in the art, it is the intention of the inventor to embody within the patent warranted hereon all changes and modifications as reasonably and properly come within the scope of his contribution to the art.

I claim as my invention:

1. A diagnostic imaging apparatus comprising:
   a scanning system adapted for scanning an examination subject for acqurinrg image information representing at least one region of said examination subject and which generates image signals corresponding to said image information;
   a signal processor, supplied with said image signals, for subjecting said image signals to spatial-frequency filtering with an adjustable bandpass characteristic to produce processed signals, said signal processor comprising at least one of the following processor means:

first processor means for entering a minimum dimension of an object of said examination subject and for setting an upper limit frequency of said bandpass characteristic at a value necessary to display said object with said minimum dimension, second processor means for entering a maximum dimension of an object of said examination subject for setting a lower limit frequency of said bandpass characteristic to a value necessary for displaying an object having said maximum dimension, third processor means for calculating spectral characteristics of noise superimposed on said image signals for setting said upper limit frequency of said bandpass characteristic dependent on the calculated spectral characteristics of the noise, and fourth processor means for entering a contour of an object of said examination subject, and including a pattern recognition stage which analyzes said image signals to identify a presence of an object having a contour corresponding to the entered contour and for, given the presence of an object having a contour corresponding to the entered contour, setting the lower limit frequency of said bandpass characteristic dependent on a smallest dimension of said object having a contour corresponding to the entered contour and a largest dimension of said object having a contour corresponding to the entered contour; and a display unit supplied with said processed signals for displaying an image of said at least one region of said examination subject.

2. A diagnostic imaging apparatus as claimed in claim 1 wherein said signal processor comprises said fourth processor means, and wherein said scanning system generates a series of images of said examination subject and wherein said signal processor selects, using identification by said pattern recognition stage of said object having a contour corresponding to the entered contour, a section in each image in said series of images to be displayed on said display unit so that said section in each image surrounding said object having a contour corresponding to the entered contour is displayed at substantially the same location in each of said images on said display unit.

3. A diagnostic imaging apparatus as claimed in claim 1 wherein said signal processor comprises said fourth processor means, and wherein said scanning system generates a series of images of said examination subject and wherein said signal processor selects, using identification by said pattern recognition stage of said object having a contour corresponding to the entered contour, a section in each image in said series of images to be displayed on said display unit so that said object having a contour corresponding to the entered contour is disposed at substantially the same location in each section of each of said images in said series, and said signal processor integrating the respective sections of the individual images in said series to form a total image represented by said processed signals supplied to said display unit.

4. A diagnostic imaging apparatus as claimed in claim 1 wherein said signal processor comprises said fourth processor means, and said apparatus further comprising a therapeutic radiation source which generates therapeutic radiation, focused to a focal zone contained in said at least one region of said examination subject, and means for activating said therapeutic radiation source to emit said therapeutic radiation only when said focal zone substantially coincides with said object having a contour corresponding to the entered contour in said image of said at least one region.

5. A diagnostic imaging apparatus as claimed in claim 4 wherein said scanning system generates a series of images of said at least one region of said examination subject, and wherein said signal processor identifies a relationship between said focal zone and said object having a contour corresponding to the entered contour in each of said images in said series.

6. A diagnostic imaging apparatus as claimed in claim 1 wherein said signal processor comprises said fourth processor means, and said apparatus further comprising a therapeutic radiation source for generating therapeutic radiation focused to a focal zone contained in said at least one region of said examination subject, and further comprising means for displacing said focal zone and said at least one region relative to each other to maintain substantial coincidence between said focal zone and said at least one region, dependent on a location in said image of said object having a contour corresponding to the entered contour.

7. A diagnostic imaging apparatus as claimed in claim 6 wherein said scanning system generates a series of images of said at least one region of said examination subject, and wherein said signal processor identifies a relationship between said focal zone and said object having a contour corresponding to the entered contour in each of said images in said series.

8. A diagnostic imaging apparatus as claimed in claim 1 wherein said scanning system comprises a radiographic scanning system having an X-ray source and an X-ray receiver disposed at opposite sides of said examination subject, said X-ray receiver generating said image signals dependent on X-rays received thereby attenuated by said examination subject.

* * * * *